United States Patent [19]

Swidler

[11] Patent Number: 5,219,980
[45] Date of Patent: Jun. 15, 1993

[54] POLYMERS BIODEGRADABLE OR BIOERODIABLE INTO AMINO ACIDS

[75] Inventor: Ronald Swidler, Palo Alto, Calif.

[73] Assignee: SRI International, Menlo Park, Calif.

[21] Appl. No.: 870,447

[22] Filed: Apr. 16, 1992

[51] Int. Cl.$^5$ .............................................. C08G 63/20
[52] U.S. Cl. ................... 528/272; 528/288; 528/289; 528/290; 528/292; 528/293; 528/295; 528/296; 528/299; 528/306; 528/307; 424/423; 424/426; 525/437
[58] Field of Search ............... 528/272, 288, 289, 290, 528/292, 293, 295, 296, 299, 306, 307; 424/423, 426; 525/437

[56] References Cited

U.S. PATENT DOCUMENTS

| | | | |
|---|---|---|---|
| 4,080,969 | 3/1978 | Casey et al. | 128/335.5 |
| 4,291,013 | 9/1981 | Wahlig et al. | 424/16 |
| 4,347,234 | 8/1982 | Wahlig et al. | 424/15 |
| 4,502,976 | 3/1985 | Heller | 252/315.4 |
| 4,525,495 | 6/1985 | Dorman et al. | 523/205 |
| 4,570,629 | 2/1986 | Widra | 128/156 |
| 4,638,045 | 1/1987 | Kohn et al. | 530/323 |
| 4,745,160 | 5/1988 | Churchill et al. | 525/415 |
| 4,888,413 | 12/1989 | Domb | 528/272 |

Primary Examiner—John Kight, III
Assistant Examiner—Sam A. Acquah
Attorney, Agent, or Firm—Hubert E. Dubb

[57] ABSTRACT

The invention presents a biodegradable polyester polymer comprising

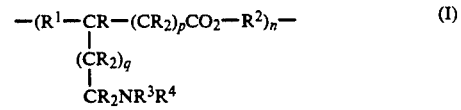

wherein: n=number of repeating polymer units of the formula shown; p=0 or 1, 0 indicating the absence of the subscripted constituent; q=0 or 1, 0 indicating the absence of the subscripted constituent; when p=0, l=1; when p=1, l=0; $R^1$=a divalent organic substituent which can include oxygen, nitrogen or sulfur atoms as part of the polymer backbone; $R^2$=a divalent organic substituent which can include oxygen, nitrogen or sulfur atoms as part of the polymer backbone; $R^3$ and $R^4$ are each independently hydrogen or an organic substituent or together form a divalent ring which may be optionally substituted; and each R is independently H, alkyl, alkenyl or alkynyl, aryl, aralkyl, cycloalkyl, cycloalkenyl or cycloalkynyl, all optionally substituted with F, Cl, Br, I, CN or $NO_2$.

4 Claims, No Drawings

POLYMERS BIODEGRADABLE OR BIOERODIABLE INTO AMINO ACIDS

TECHNICAL FIELD

The invention relates to a class of polyester polymers having $\beta$ amino acid repeating units and which will readily hydrolyze under physiological conditions. Such polymer systems are useful for drug delivery, as absorbable sutures and as dissolvable wound dressings. They can also serve to provide temporary polymeric layers or coatings which hydrolyze and thereby dissipate with time. Such coatings have numerous uses from temporary protection of metal and other surfaces to masking during semiconductor processing operations.

BACKGROUND OF THE INVENTION

A number of bioerodible or biodegradable polymers are known and are useful for controlled release of pharmaceuticals. Such polymers are described in, for example, U.S. Pat. No. 4,291,013, issued Sep. 22, 1981 to H. Wahlig, et al, U.S. Pat. No. 4,347,234, issued Aug. 31, 1982 to H. Wahlig, et al, U.S. Pat. No. 4,525,495, issued Jun. 25, 1985 to L.C. Dorman, et al, U.S. Pat. No. 4,570,629, issued Feb. 18, 1986 to A. Widra, U.S. Pat. No. 4,572,832, issued Feb. 25, 1986 to K. Kigasawa, et al, U.S. Pat. No. 4,587,268, issued May 6, 1986 to R.W. Pfirrmann, U.S. Pat. No. 4,638,045, issued Jan. 20, 1987 to J. Kohn, et al, U.S. Pat. No. 4,675,381, issued Jun. 23, 1987 to D. Bitchon, and U.S. Pat. No. 4,745,160, issued May 17, 1988 to J.R. Churchill, et al. Of particular interest is Kohn, et al U.S. Pat. No. 4,638,045 which utilizes non-peptide bonds between side chains on dipeptides with the side chains being bonded together by hydrolytically unstable bonds which are biodegradable. The products of hydrolysis of such compounds include the side chains of each monomer unit and are, therefore, not as fully biocompatible as might be desired.

The present invention is directed to overcoming one or more of the problems as set forth above.

DISCLOSURE OF INVENTION

In accordance with the present invention a biodegradable polyester polymer is set forth comprising

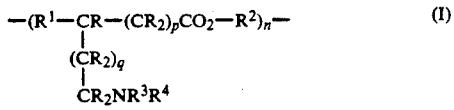

wherein:
n = number of repeating polymer units of the formula shown;
p = 0 or 1, 0 indicating the absence of the subscripted constituent;
q = 0 or 1, 0 indicating the absence of the subscripted constituent;
when p=0, q=1;
when p=1, q=0;
$R^1$ = a divalent organic substituent which can include oxygen, nitrogen or sulfur atoms as part of the polymer backbone;
$R^2$ = a divalent organic substituent which can include oxygen, nitrogen or sulfur atoms as part of the polymer backbone;
$R^3$ and $R^4$ are each independently hydrogen or an organic substituent which may be optionally substituted with O, S, or N or together form a divalent organic ring which may be optionally substituted with O, S, or N; and each R is independently H, alkyl, alkenyl or alkynyl, aryl, aralkyl, cycloalkyl, cycloalkenyl or cycloalkynyl, all optionally substituted with F, Cl, Br, I, CN, or $NO_2$.

A polymer as set forth above is directly biodegradable into lower molecular weight components of the nature of $\beta$ amino acids or substituted amino acids which are highly biocompatible. Biodegradation of the polymer is via hydrolysis of the ester linkage. This can take place readily at pH about 8 or below through the formation of a six membered ring intermediate form.

Pharmaceuticals can be incorporated into a matrix made of such a polymer and the matrix can be attached as a patch to the body, used as a pill, used as a lozenge, used as a suppository or otherwise contacted with the body whereupon on hydrolysis of the polyester linkage the pharmaceutical is released into the body while the only components of the hydrolysis are the $\beta$ amino acids which form the polymer chain. The polymers of the invention can also be used to form temporary polymer films which dissolve over a period of time as the polymers are hydrolyzed. Such films can be used, for example, as wound dressings. The polymers can also be used to formulate sutures and such sutures will dissolve away in time. The products of the hydrolysis are usually highly biocompatible. The polymers can also be used as resists or for masking purposes, for example, for semiconductor processing. They can also be used as temporary protective coatings for metals or other materials, particularly when it is desirable to be able to dissolve the coatings away after a period of protection.

BEST MODE FOR CARRYING OUT INVENTION

In accordance with the present invention a biodegradable polyester polymer of formula I is set forth. The polymer is characterized in that it is a polyester and in that it hydrolyses via a zero order reaction, analogously to the hydrolysis of esters of $\beta$-alanine as reported at Beilstein 4, 402-3, to form $\beta$ amino acids. It is essential that the biodegradable polyester polymer hydrolyze into amino acids since in that situation proton catalyzed hydrolysis takes place at pH values of about 8 and below, e.g., at physiological pH, relatively readily via a zero order reaction since a six membered ring can be formed via hydrogen bonding of the protonated (at pH 8 and below) hydrogen of the amino group to the oxygen of the carbonyl group whereby the carbonyl group is readily hydrolyzed by water to form the acid and the corresponding alcohol. The defined values of the subscripts p and q are such that six membered rings are formable. Thus, the preferred polymers of the invention can be represented by the formulas:

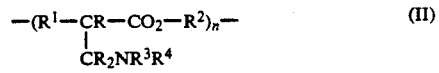

and

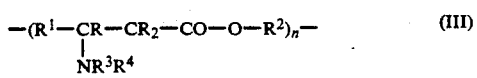

The degree of polymerization, represented by the value of n, is not critical. Usually, n will be chosen such that the molecular weight of the polymer will fall within a range from about 500 to about 5,000. However, the invention is not limited to n values and/or to molecular weights within this range. $R^1$ and $R^2$ are each independently a divalent organic substituent which can include oxygen, nitrogen or sulfur atoms as part of the polymer backbone. Examples of usable $R^1$ and $R^2$ substituents are set forth below.

$R^3$ and $R^4$ are each independently hydrogen or an organic substituent which may be optionally substituted with O, S or N or together form a divalent ring which may be optionally substituted with O, S or N An examples of such a divalent ring is set forth below.

Each R can independently be any of H, alkyl, alkenyl or alkynyl, aryl, aralkyl, cycloalkyl, cycloalkenyl or cycloalkynyl, all optionally substituted with F, Cl, Br, I, CN, or $NO_2$. For very ready hydrolysis each R can be hydrogen, methyl or ethyl.

The sizes of the R, $R^1$, $R^2$, $R^3$ and $R^4$ constituents and their structures and chemical makeup can be chosen so as to provide a desired rate of hydrolysis. If these groups are large they will lead to relatively slow hydrolysis since accessibility of the ester linkage being hydrolyzed will be limited by the rate of diffusion of water and hydrogen ion through the polymer. Conversely, if the groups are small the hydrolysis rate will generally be large.

While the polymer of the present invention is a biodegradable polyester polymer in structure it may be made by any of a number of procedures. The polymers can be synthesized from polyester polymers having double bonded carbon atoms in the polymer backbone attached to, or one carbon removed from, the carbonyl of the ester linkage. The polyester polymers can themselves be prepared by methods known to the art, for example by reacting an acid or anhydride having a double bond with a polyol, for example a diol. This can be represented with maleic anhydride and substituted maleic anhydrides by the reaction scheme:

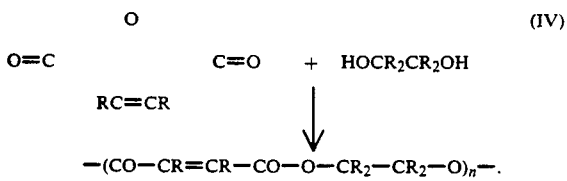

$$-(CO-CR=CR-CO-O-CR_2-CR_2-O)_n-.$$

An additional $CR_2$ group can be present between one of the C=O groups and the adjacent =CR group, taking into account the requirement that a six membered ring be formable to promote hydrolysis.

A useful synthesis of the biodegradable or bioerodible polymers of the invention consists of reacting the double bonds in the intermediate polyester polymer (IV) with an amine of the formula $NRR^3R^4$ by the well known Michael reaction. The reaction will often be carried out by mildly heating the reactants, for example, at a temperature of 30° C. to 150° C. However, dependant upon the particular reactants chilling to below room temperature may be desirable. The time of reaction an also be varied dependant upon the particular reactants, all in accordance with the vast literature describing the Michael reaction.

For example, a polymaleic acid polymer may be formed by reacting maleic anhydride with 1,2-dihydroxyethane at a temperature of above about 100° C. until sufficient water has been evolved (the water is generally removed by distillation as it is formed) to form the intermediate polyester polymer (IV) which is then reacted with a group $NRR^3R^4$ as set forth above. The resulting amine containing polyester polymer (III) of the invention then has a structure which allows A six membered ring to be formed. If one desires to make the β type polyester polymer of the formula (II), itaconic acid or the anhydride thereof, or a substituted itaconic acid or anhydride, is substituted for the maleic anhydride. Alternatively, the biodegradable amine substituted polyester polymer (II) or (III) of the present invention may be made by carrying out the Michael reaction on maleic acid or itaconic acid or the corresponding anhydride or on a derivative thereof to form an N,N dialkyl, etc., derivative followed by esterification (reaction with a diol) to form the desired polymer.

Pharmaceuticals or other slow release compounds, for example, pesticides, can be incorporated in the polyester polymers (I) by including them in solution during the polymerization reaction via which the polymer of the invention or a precursor polymer are formed. The particular pharmaceuticals must naturally not react with the polymer leading to significant loss of activity or to produce undesirable or toxic substances.

It should be noted that some of the substituents suggested as possible for the groups R, $R^1$, $R^2$, $R^3$ and $R^4$ are such as might make the degradation products not as biocompatible as might be desirable. However, when such substituents are present the polyester polymer can be utilized for purposes other than delivery of pharmaceuticals over a period of time. For example, they can be used to form temporary protective films which biodegrade away in a desirable period of time.

The invention will be better understood by reference to the following illustrative examples.

EXAMPLE 1

This example describes the synthesis of a γ amino acid type polyester polymer of the formula (I) in accordance with the present invention.

To a 250 mL round bottom flask were charged 26.02 g (200 millimoles) of itaconic acid, 28.84 g (200 millimoles) of trans-cyclohexanedimethanol, mL of toluene, 100 mg of p-toluene sulfonic acid and 100 mg of Antioxidant 330 (a trademark of Ethyl Corporation). The flask was equipped with a magnetic stirring bar, a distillation condenser and a Dean-Stark receiver. The reaction flask was heated at 150° C. until 7.2 mL of water were collected in the receiver. The solution was cooled at room temperature and was added dropwise to 500 mL of methanol with vigorous stirring. The precipitate was dried in a vacuum oven. The yield of polymer was 42.36 g (89%).

A portion of the polymer, 5 g (21 millimoles) and a molar excess, namely, 5 g (57 millimoles) of morpholine, were dissolved in 20 mL of methylethylketone. The solution was heated at 60° C. for 2 hours. After cooling to room temperature the solution was added dropwise to 500 mL of methanol. The resulting precipitate was dried in a vacuum oven. NMR of the resulting polymer indicated that no vinyl protons were present and that there was a strong signal corresponding to the structure:

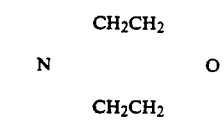

EXAMPLE 2

This example demonstrates the biodegradability or bioerodibility of the polymer of Example 1.

An aliquot of the final polymer product of Example 1 was checked for solubility in aqueous media. When the pH of the aqueous solution was 3.6 or less the polymer readily dissolved.

EXAMPLE 3

This example demonstrates how to produce a β amino acid type polyester polymer of the formula (II) in accordance with the present invention.

A polymaleic acid polymer is formed by reacting substantially equimolar quantities of maleic anhydride and 1,2-dihydroxy ethane to form an intermediate polyester polymer. The intermediate polymer is then reacted with a group $NRR^3R^4$. The resulting amine containing polyester polymer has a structure which allows a six membered ring to be formed. As a result, protonation leads to hydrolysis (and hence dissolution) at a pH of about 8 or below and the polymer bioerodes and/or biodegrades.

EXAMPLE 4

The biodegradable polymer in accordance with any of Examples 1-3 has incorporated therein one or more pharmaceuticals and is formulated into a patch which is implanted into a human patient. The patch dissolves over a period of time at physiological pH (about 7) and the pharmaceutical is released into the patient during that time.

EXAMPLE 5

A biodegradable polyester polymer in accordance with any of Examples 1-3 is utilized as a film on a wound for the purpose of protection. After a period of time it has biodegraded and is no longer present.

EXAMPLE 6

A biodegradable polyester polymer in accordance with any of Examples 1-3 is utilized as a resist for semiconductor processing. After use it is stripped utilizing a solution at pH 8 or below.

INDUSTRIAL APPLICABILITY

The present invention provides a biodegradable polyester polymer in which pharmaceuticals can be dispersed and which will biodegrade over a period of time under physiological conditions to release such pharmaceuticals.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A biodegradable polyester polymer, comprising:

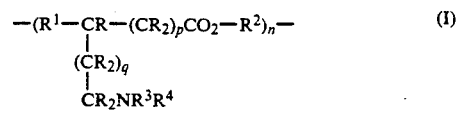

wherein:
n = number of repeating polymer units of the formula shown;
p = 0 or 1, 0 indicating the absence of the subscripted constituent;
q = 0 or 1, 0 indicating the absence of the subscripted constituent;
when p=0, q=1;
when p=1, q=0;
$R^1$ = a divalent organic radical optionally substituted with oxygen, nitrogen or sulfur atoms as part of the polymer backbone;
$R^2$ = a divalent organic radical optionally substituted with oxygen, nitrogen or sulfur atoms as part of the polymer backbone;
$R^3$ and $R^4$ are each independently hydrogen or an organic substituent which may be optionally substituted with O, S or N or together form a divalent ring which may be optionally substituted with O, S or N; and
each R is independently H, alkyl, alkenyl or alkynyl, aryl, aralkyl, cycloalkyl, cycloalkenyl or cycloalkynyl, all optionally substituted with F, Cl, Br, I, CN or $NO_2$.

2. A polymer as set forth in claim 1, wherein each R=H, methyl or ethyl.

3. A biodegradable polyester polymer, comprising:

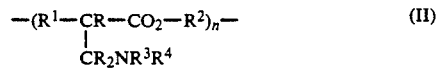

or

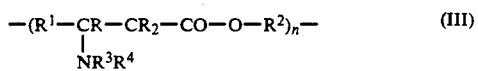

wherein:
n = number of repeating polymer units of the formula shown;
$R^1$ = a divalent organic radially optionally substituted with oxygen, nitrogen or sulfur atoms as part of the polymer backbone;
$R^2$ = a divalent organic radical optionally substituted with oxygen, nitrogen or sulfur atoms as part of the polymer backbone;
$R^3$ and $R^4$ are each independently hydrogen or an organic substituent which may be optionally substituted with O, S or N or together form a divalent ring which may be optionally substituted with O, S or N; and
each R is independently H, alkyl, alkenyl or alkynyl, aryl, aralkyl, cycloalkyl, cycloalkenyl or cycloalkynyl, all optionally substituted with F, Cl, Br, I, CN or $NO_2$.

4. A polymer as set forth in claim 3, wherein each R=H, methyl or ethyl.

* * * * *